(12) United States Patent
Hasegawa et al.

(10) Patent No.: US 7,988,620 B2
(45) Date of Patent: Aug. 2, 2011

(54) CAPSULE ENDOSCOPE APPARATUS

(75) Inventors: Jun Hasegawa, Hino (JP); Hirokazu Nishimura, Hachioji (JP); Hideki Tanaka, Hino (JP); Ryoko Inoue, Hachioji (JP)

(73) Assignee: Olympus Corporation, Tokyo (JP)

( * ) Notice: Subject to any disclaimer, the term of this patent is extended or adjusted under 35 U.S.C. 154(b) by 1388 days.

(21) Appl. No.: 11/485,563

(22) Filed: Jul. 12, 2006

(65) Prior Publication Data

US 2006/0252987 A1 Nov. 9, 2006

Related U.S. Application Data

(63) Continuation of application No. PCT/JP2005/000342, filed on Jan. 14, 2005.

(30) Foreign Application Priority Data

Jan. 14, 2004 (JP) ................................. 2004-007379

(51) Int. Cl.
*A61B 1/00* (2006.01)
*A61B 1/04* (2006.01)
(52) U.S. Cl. ....................................... 600/117; 600/118
(58) Field of Classification Search .................. 600/109, 600/117, 118, 160
See application file for complete search history.

(56) References Cited

U.S. PATENT DOCUMENTS

| 7,463,918 | B2* | 12/2008 | Kim et al. | 600/407 |
| 2002/0173718 | A1* | 11/2002 | Frisch et al. | 600/424 |
| 2002/0198439 | A1 | 12/2002 | Mizuno | |
| 2002/0198470 | A1* | 12/2002 | Imran et al. | 600/587 |
| 2003/0023150 | A1* | 1/2003 | Yokoi et al. | 600/300 |
| 2003/0073935 | A1* | 4/2003 | Segawa et al. | 600/593 |
| 2003/0085994 | A1 | 5/2003 | Fujita et al. | |
| 2003/0114742 | A1* | 6/2003 | Lewkowicz et al. | 600/407 |
| 2003/0229268 | A1 | 12/2003 | Uchiyama et al. | |

FOREIGN PATENT DOCUMENTS

| JP | 7-111985 | 5/1995 |
| JP | 11-325810 | 11/1999 |
| JP | 2002-159472 | 6/2002 |
| JP | 2003-019111 | 1/2003 |
| JP | 2003-070728 | 3/2003 |
| JP | 2003-116781 | 4/2003 |
| JP | 2003-135389 | 5/2003 |
| JP | 2003-299612 | 10/2003 |
| JP | 2003-325438 | 11/2003 |
| WO | WO 01/87377 A2 | 11/2001 |
| WO | WO 03/001966 A2 | 1/2003 |

* cited by examiner

*Primary Examiner* — Philip R Smith
(74) *Attorney, Agent, or Firm* — Scully, Scott, Murphy & Presser, P.C.

(57) ABSTRACT

A signal processing circuit of an external device includes a CPU and a memory which are not shown. A program for estimating at least one of the position and orientation of a capsule endoscope on the basis of strength signals received through respective antennas is installed in the signal processing circuit. A single-core coil to generate a magnetic field is arranged in the capsule endoscope. The generated magnetic field is detected by a plurality of coils arranged outside a body, whereby a distance that the capsule endoscope has traveled can be obtained with accuracy. This arrangement controls image-capture timing to reliably capture images necessary for a diagnosis and prevent unnecessary image capture.

3 Claims, 13 Drawing Sheets

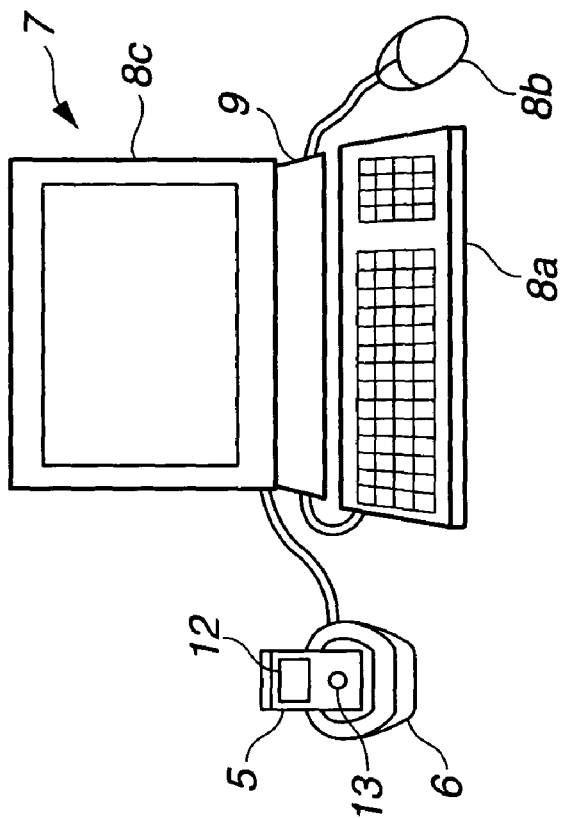
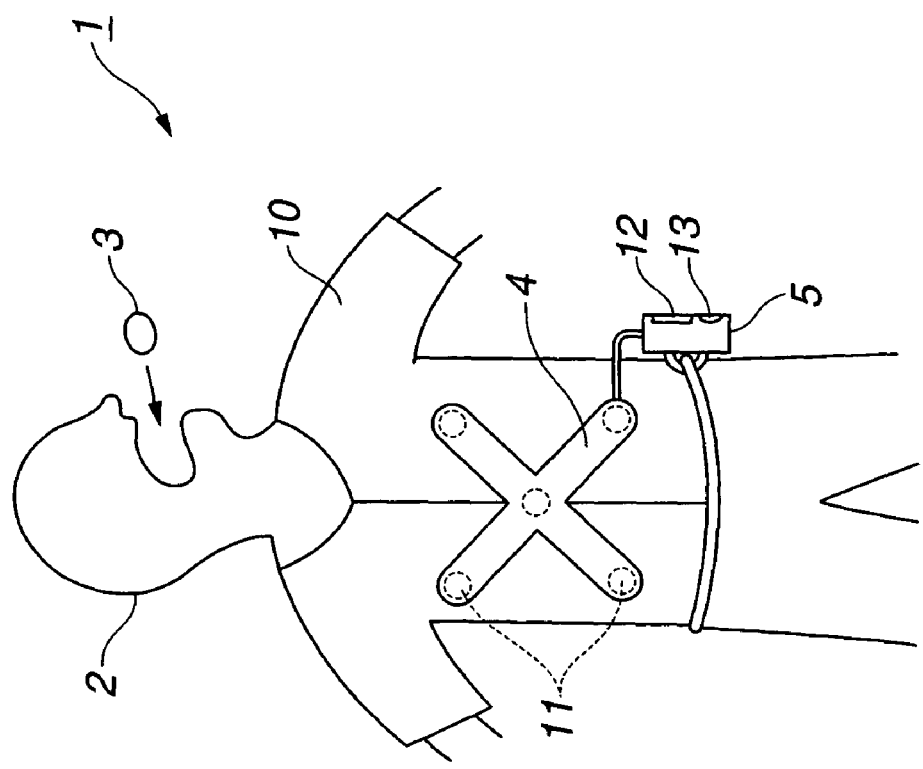

DISPLAYING IMAGES PRECEDING IMAGE In

CAPSULE ENDOSCOPE APPARATUS

CROSS REFERENCE TO RELATED APPLICATION

This application is a continuation application of PCT/JP2005/000342 filed on Jan. 14, 2005 and claims benefit of Japanese Application No. 2004-007379 filed in Japan on Jan. 14, 2004, the entire contents of which are incorporated herein by this reference.

BACKGROUND OF THE INVENTION

1. Field of the Invention

The present invention relates to a capsule endoscope apparatus comprising an ingestible capsule unit and an extracorporeal unit for receiving biological information transmitted from the capsule unit.

2. Description of the Related Art

In recent years, capsule endoscope apparatuses for conducting an examination and the like in a body cavity with an ingested capsule type unit have been proposed.

For example, Japanese Unexamined Patent Application Publication No. 7-111985 discloses an apparatus including a spherical capsule divided in two having communication means for transmitting biological information to an extracorporeal device.

PCT Publication No. WO 01/87377 A2 discloses a capsule endoscope apparatus for detecting the motion (rate) of a capsule unit through an acceleration sensor or the like disposed in the capsule unit to control a capture rate or a display rate on the basis of a detected value.

SUMMARY OF THE INVENTION

The present invention provides a capsule endoscope apparatus including an image capturing unit for capturing an image in a body to transmit the image by radio and a receiving unit for receiving the image transmitted by radio from the image capturing unit to record the image, the apparatus further including: an estimating unit for receiving a signal transmitted by radio from the image capturing unit through each of a plurality of antennas arranged at different positions outside the body to estimate at least one of the position and orientation of the image capturing unit on the basis of the signals received through the antennas; and a control unit for controlling image capture by the image capturing unit using information regarding at least one of the position and orientation estimated by the estimating unit.

BRIEF DESCRIPTION OF THE DRAWINGS

FIG. 1A and FIG. 1B include explanatory diagrams showing the structure of a capsule endoscope apparatus according to a first embodiment of the present invention and that of an extracorporeal device, such as an extracorporeal terminal, FIG. 1A being the explanatory diagram showing the capsule endoscope apparatus, FIG. 1B being the explanatory diagram showing the structure of the extracorporeal device, such as an extracorporeal terminal.

DETAILED DESCRIPTION OF THE PREFERRED EMBODIMENT(S)

Figure 2:
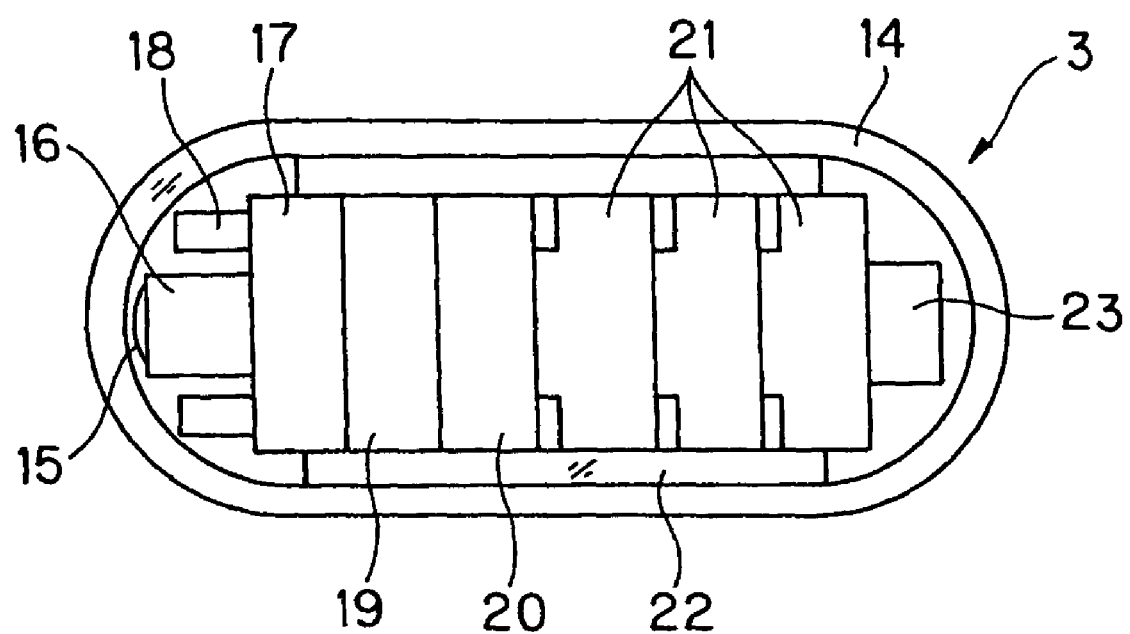
FIG. 2 is an explanatory diagram showing the internal structure of a capsule endoscope shown in FIG. 1A.

Embodiments of the present invention will now be described below with reference to the drawings.

First Embodiment

Structure

FIG. 1A is an explanatory diagram showing the entire structure of a capsule endoscope apparatus 1 according to the present embodiment. Referring to FIG. 1A, the capsule endoscope apparatus 1 includes a capsule endoscope 3, ingested by a patient 2, for examining a patient's body cavity and an external device 5 disposed outside the body of the patient 2, the external device 5 serving as a receiver connected to an antenna unit 4 for receiving image information captured by the capsule endoscope 3 by radio.

According to the present embodiment, the image information, transmitted from the capsule endoscope 3 and received by the external device 5, is recorded on portable memory means, e.g., a Compact Flash (registered trademark) memory, which will be described later, installed in the external device 5 during the examination of the body cavity. Alternatively, the image information is downloaded into a terminal 7, e.g., a personal computer, through a USB cable or the like (not shown). In addition, placing the external device 5 on a cradle 6 electrically connects the external device 5 to the terminal 7.

When viewer software for observation is executed in the terminal 7 shown in FIG. 1B, the image information stored in the external device 5 can be downloaded into a terminal body 9 by operating an input control device, such as a keyboard 8a or a mouse 8b, whereby downloaded images can be displayed on a monitor 8c.

As shown in FIG. 1A, in a case where the patient 2 swallows the capsule endoscope 3 for endoscopy, the antenna unit 4 including a plurality of antennas 11 is attached to a jacket 10 that the patient 2 wears. The antenna unit 4 receives signals, which are obtained by image capture through the capsule endoscope 3 and are transmitted from an antenna 23 (refer to FIG. 2) built in the capsule endoscope 3. The external device 5, connected to the antenna unit 4, can store captured images. The external device 5 is attached to, e.g., a belt of the patient 2 through a hook detachable from the belt. The antenna unit 4 may be stuck directly on the patient's body.

Figure 3:
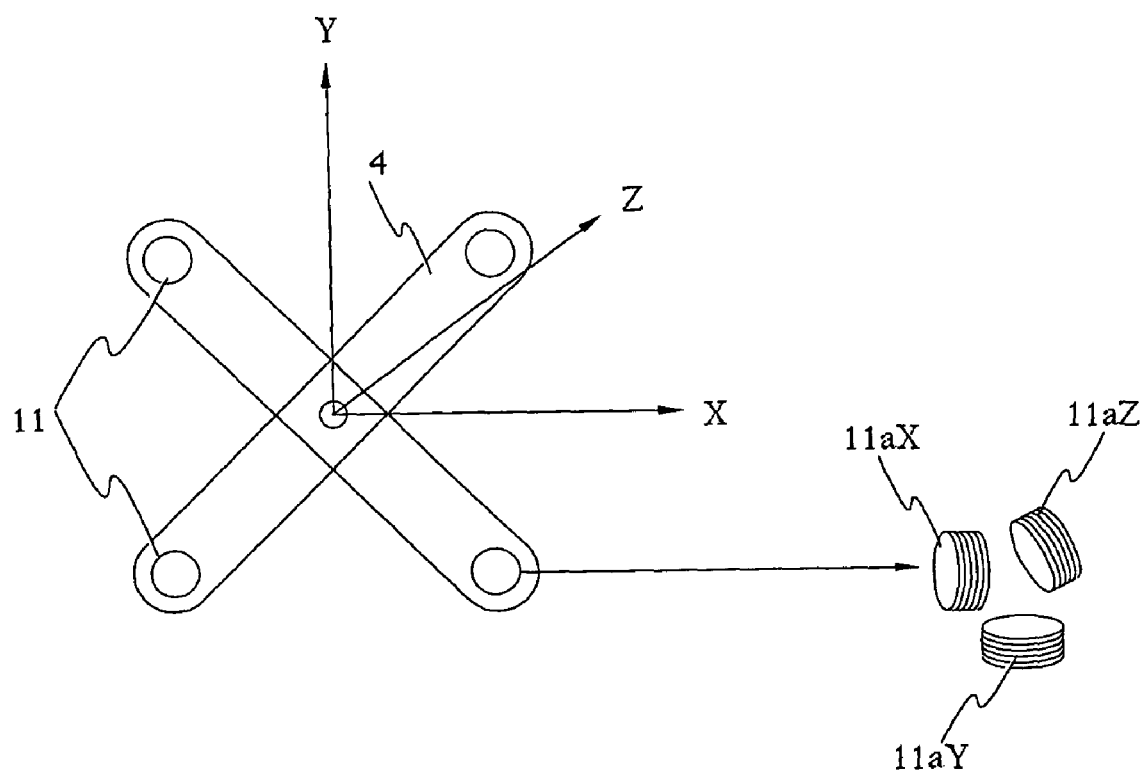
FIG. 3 is an explanatory diagram showing single-core coils serving as antennas of an antenna unit in FIG. 1A.

In the antenna unit 4, each antenna 11 includes single-core coils different in position and orientation. For example, single-core coils 11aX, 11aY, . . . , 11dY, and 11dZ aligned with the coordinate axes representing X, Y, and Z coordinates as shown in FIG. 3 are available.

The external device 5 has, e.g., a box shape. The front face thereof incorporates a liquid crystal monitor 12 for image display and an operation section 13 for instructions and operations.

Alternatively, the external device 5 may include an LED for alarm display and a power switch alone, the alarm display being concerned with the remaining amount of a battery, the power switch serving as the operation section 13. In this case, a portable display (viewer), which is not shown, for processing image signals transmitted from the capsule endoscope 3 to display images on a liquid crystal monitor equipped therewith may be connected as a second external device to the external device 5.

Referring to FIG. 2, the capsule endoscope 3 includes an outer housing 14 shaped in a cylinder, whose rear end is closed, and a substantially semispherical, i.e., domed cover 14a connected to the front end of the cylinder with an adhesive to provide a capsule structure. Accordingly, the capsule endoscope 3 has a watertight structure.

In the domed cover 14a that is transparent, an objective lens 15 for forming an image of incident light received through the domed cover 14a is attached to a lens frame 16 such that the objective lens 15 is positioned in the center of the section of the cylinder. An image capturing element, e.g., a CCD imager 17 is disposed in the image forming position of the objective lens 15.

As an illumination system, e.g., four white LEDs 18 are arranged around the objective lens 15 on the same plane.

In addition, a processing circuit 19 for driving the white LEDs 18 to emit light and driving the CCD imager 17 to execute a process of generating image signals from signals captured by the CCD imager 17, a communication processing circuit 20 for transmitting the image signals, and button batteries 21 for supplying power to the circuits 19 and 20 are arranged on, e.g., the rear of the CCD imager 17 within the outer housing 14.

On the rear of the button batteries 21, i.e., in the other semispherical end, the antenna 23 for transmitting and receiving radio waves is arranged so as to connect to the communication processing circuit 20. The CCD imager 17, the white LEDs 18, and the circuits are mounted on respective substrates (not shown) and the substrates are connected via a flexible substrate.

In the capsule endoscope 3, the processing circuit 19 generates a control signal to control image-capture timing of the CCD imager 17. In normal image capture, two frame images are captured per second. In a region, such as esophagus, where the capsule endoscope moves at a relatively high rate, e.g., 15 to 30 frame images are captured per second. The antenna 23 receives a signal transmitted from the external device 5. The communication processing circuit 20 processes the received signal and supplies the resultant signal to the processing circuit 19. The processing circuit 19 controls image-capture timing of the CCD imager 17 and turn-on/off of the white LEDs 18 in response to the supplied signal.

Operation

Figure 4:
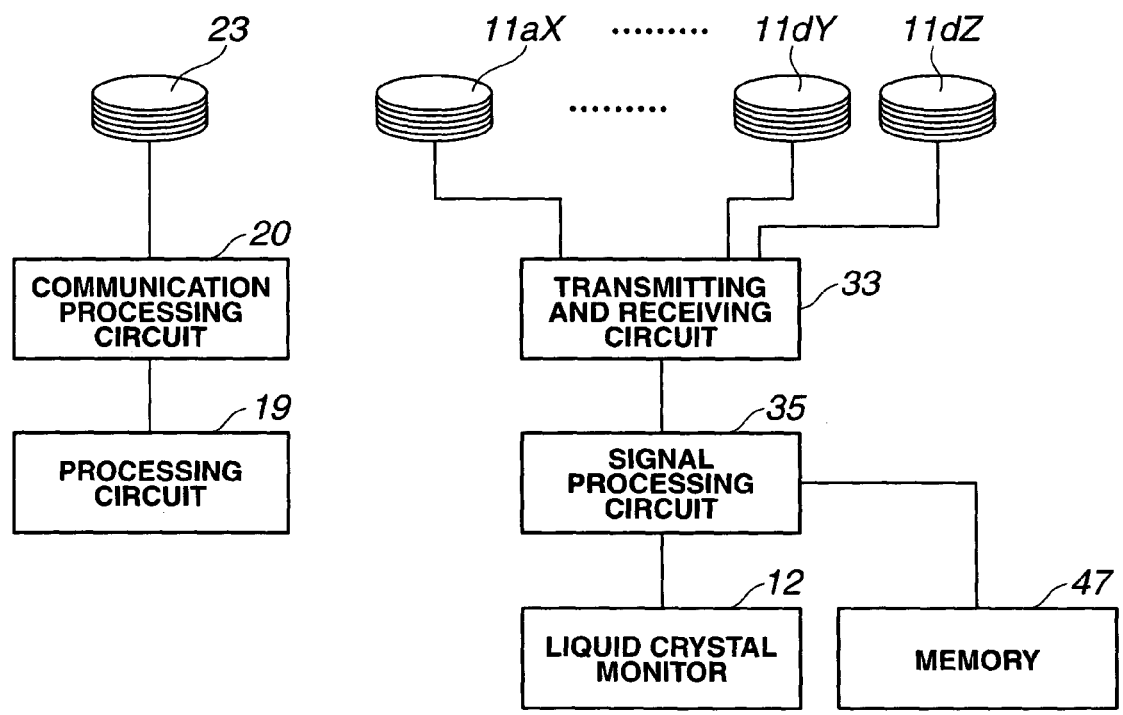
FIG. 4 is an explanatory diagram showing the structure of a signal transmitting and receiving function for an antenna of the capsule endoscope of FIG. 2 and that for the antennas of the antenna unit in FIG. 1.
Figure 5:
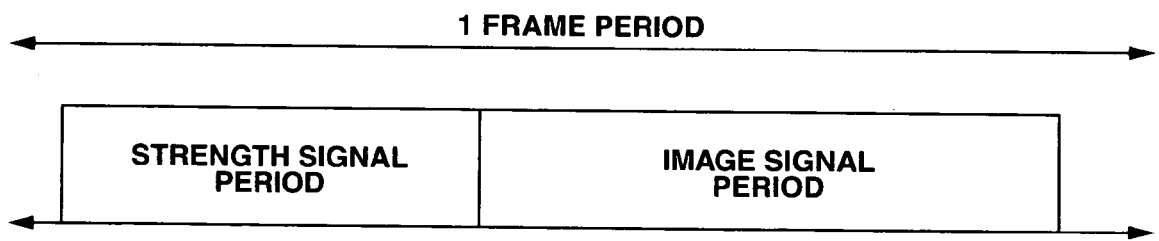
FIG. 5 is a diagram explaining signals transmitted from the antenna of the capsule endoscope of FIG. 2.

In the capsule endoscope 3, as shown in FIG. 4, the processing circuit 19 outputs an image signal and a signal indicative of a signal strength which are shown in FIG. 5. The communication processing circuit 20 transmits the signals at a predetermined radio-field intensity through the antenna 23 to the external device 5. In the external device 5, a transmitting and receiving circuit 33 receives the signals through each of the antennas 11ax, 11aY, . . . , 11dY, and 11dZ of the antenna unit 4.

The transmitting and receiving circuit 33 supplies the image signals and the strength signals to a signal processing circuit 35. The signal processing circuit 35 compares the strengths of the strength signals received through the respective antennas 11ij. Consequently, the signal processing circuit 35 detects the antenna most suitable to receive the image signal transmitted from the capsule endoscope 3. The signal processing circuit 35 supplies the image signal received through the most suitable antenna to memory means 47, such as a Compact Flash (registered trademark) memory (CF memory) or a hard disk, connected to the signal processing circuit 35 to store the image signal. Furthermore, the signal processing circuit 35 supplies the image signal received through the most suitable antenna to the liquid crystal monitor 12 connected to the signal processing circuit 35 to display an image captured through the capsule endoscope.

In the external device 5, the signal processing circuit 35 includes a CPU and a memory, which are not shown. A program for estimating the position and orientation of the capsule endoscope 3 on the basis of the strength signals received through the antennas 11ij is installed in the signal processing circuit 35. The position and orientation thereof can be estimated using a method for solving a plurality of nonlinear equations disclosed in Japanese Unexamined Patent Application Publication No. 11-325810. The signal processing circuit 35 obtains 12 nonlinear equations, in which the positions and orientations of the single-core coils arranged in the capsule endoscope 3 are unknown, from the strength levels of the strength signals received through the antennas 11ax, 11aY, . . . , 11dY, and 11dZ. The 12 nonlinear equations are solved by iterative refinement, e.g., the Gauss-Newton method, whereby the position and orientation of the capsule endoscope 3 is estimated. The estimated position and orientation are represented by coordinate values with respect to the antenna unit 4 in FIG. 3. The coordinate values are stored together with the image signal in the memory means 47. It is, however, unnecessary to estimate both of the position and the direction. Either of them may be estimated.

Figure 6:
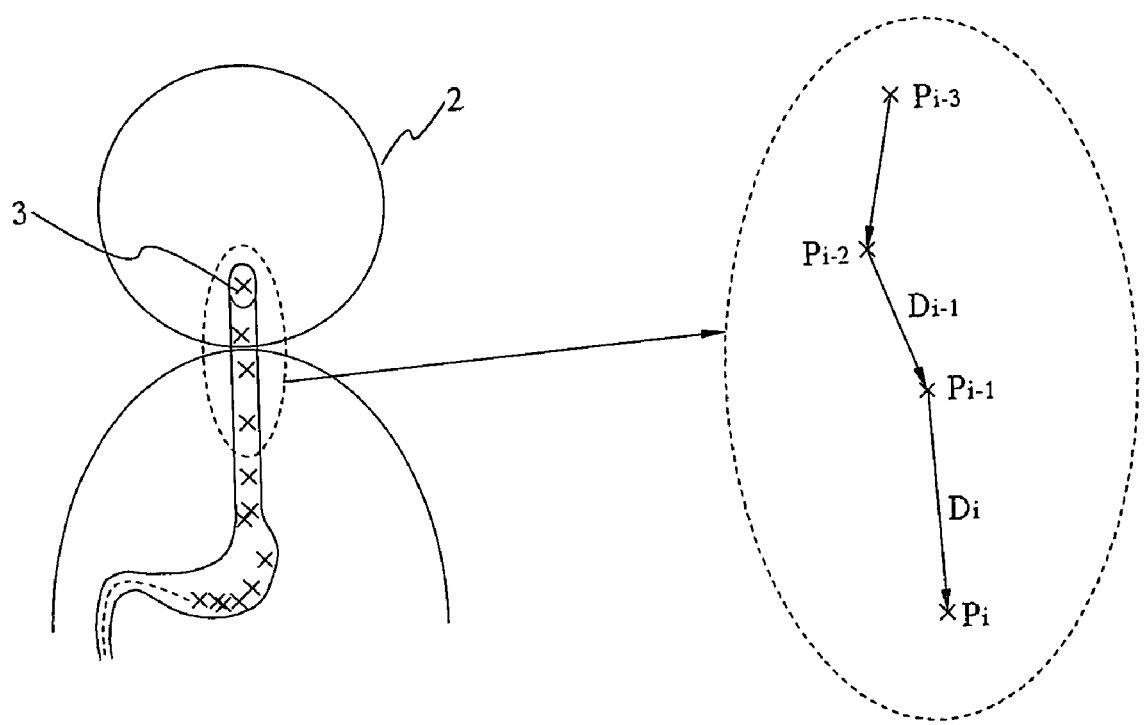
FIG. 6 is a first diagram explaining a process by a signal processing circuit in FIG. 4.

Assuming that the position of the capsule endoscope 3 is represented by Pi(Xi, Yi, Zi) as shown in FIG. 6, a distance Di that the capsule endoscope 3 has traveled is obtained by the following Expression.

$$Di = \{(Xi-1-Xi)^2 + (Yi-1-Yi)^2 + (Zi-1\ Zi)^2\}^{1/2} \quad (1)$$

When the distance Di that the capsule endoscope 3 travels is small, there is a high possibility that images in the same field of view may be captured. Accordingly, image-capture timing of the CCD imager 17 in the capsule endoscope 3 is set to a low rate. For example, in the case of capturing two frame images per second (Ti=1/2[s]), the timing is changed to a rate at which one frame image is captured per second (Ti=1/1[s]). Image-capture timing Ti[s] can be calculated by the following Expression using the distance Di.

$$Ti = \alpha/Di[s] \quad (2)$$

where $\alpha$ is a constant.

In the signal processing circuit 35 of the external device 5, the CPU obtains the image-capture timing Ti[s]. The signal processing circuit 35 supplies a signal indicating the obtained image-capture timing to the transmitting and receiving circuit 33. The transmitting and receiving circuit 33 transmits the signal to the capsule endoscope 3 through the proper antenna 11*ij* (i.e., transmits the signal indicating the image-capture timing through the above-described determined antenna most suitable to receive the image signal).

In the capsule endoscope 3, the antenna 23 receives the signal indicating the image-capture timing transmitted from the antenna 11*ij* connected to the external device 5'. The received signal is supplied to the processing circuit 19 via the communication processing circuit 20. The processing circuit 19 supplies a signal to control image capture to the CCD imager 17 in response to the supplied signal indicating the image-capture timing.

Figure 7:
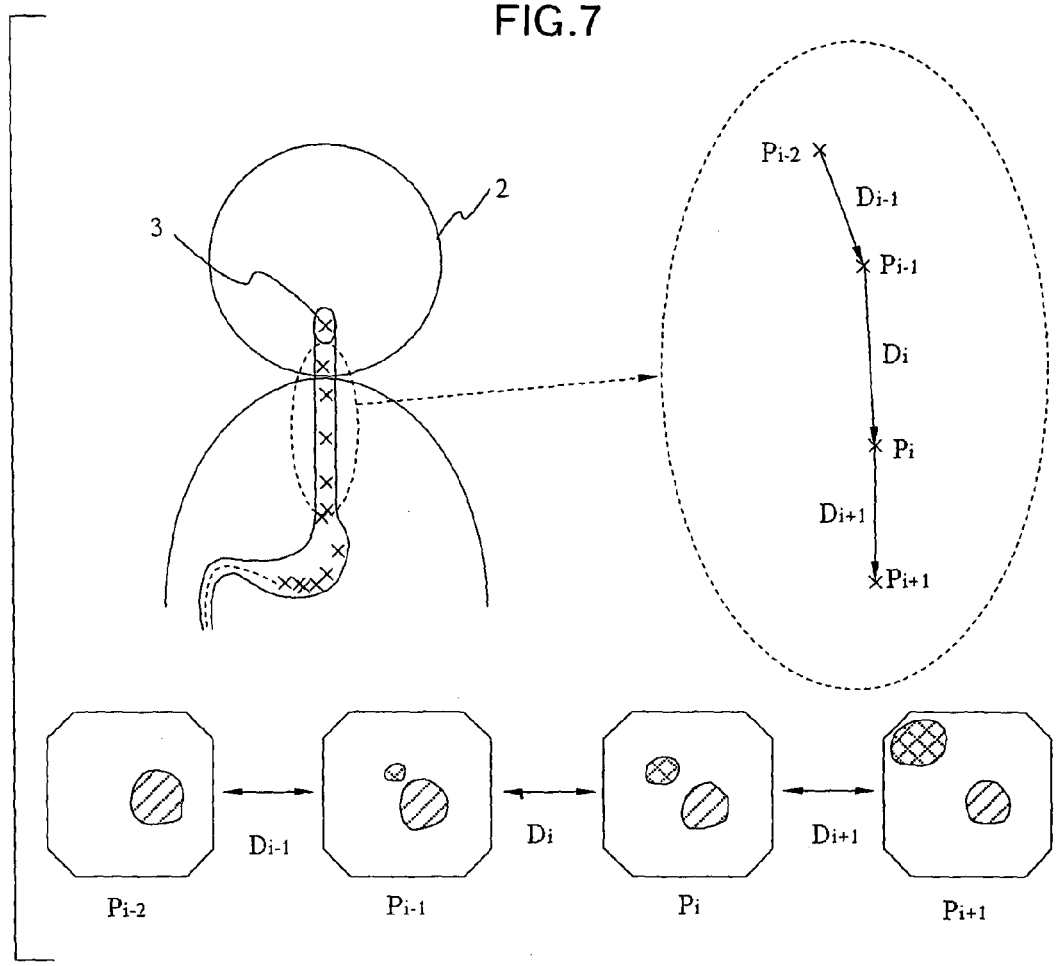
FIG. 7 is a second diagram explaining the process by the signal processing circuit in FIG. 4.

As for the constant α in Expression (2) to obtain the image-capture timing, images and positional information sets of a plurality of patients are collected and the constant α is derived from distances of the capsule endoscope 3 between the collected images. For instance, as shown in FIG. 7, images Pi−1 to Pi+1 including the same subject are detected from the collected images, the same subject being moved from the center to a peripheral portion in the images. A distance D (=Di+Di+1) that the capsule endoscope 3 has traveled in this case is obtained. When the distance that the capsule endoscope 3 has traveled is larger than the distance D, sections which are not captured as images may exist between sections corresponding to the images. Therefore, a coefficient for a is set so that at least one frame image is captured in the distance D. The distance D may be obtained from the average Davr of a plurality of samples.

Advantages

According to the present embodiment, the single-core coil for generating a magnetic field is arranged in the capsule endoscope 3 and the generated magnetic field is detected by the plurality of coils disposed outside the body, so that the accurate distance that the capsule endoscope 3 has traveled can be obtained. Since the image-capture timing of the CCD imager 17 can be changed on the basis of the accurate distance in the present embodiment, a user can efficiently confirm a diagnosis using images.

Second Embodiment

Figure 8:
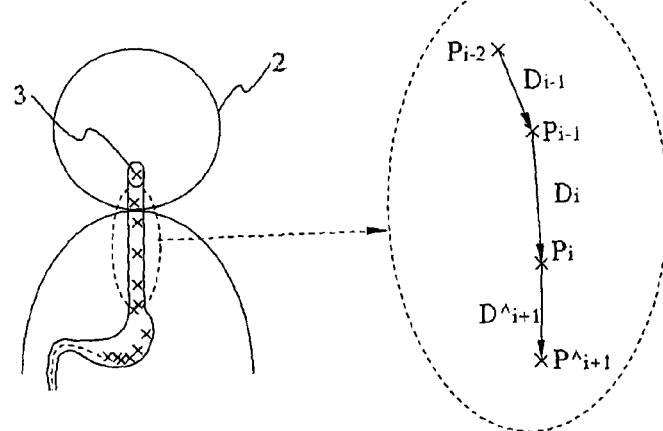
FIG. 8 is a diagram explaining a process by a signal processing circuit according to a second embodiment of the present invention.

FIG. 8 is a diagram explaining a process by a signal processing circuit according to a second embodiment of the present invention.

Structure

The structure of an apparatus according to the second embodiment is identical to that according to the first embodiment with the exception that a program, installed in a CPU of an external device 5 in the second embodiment, for obtaining image-capture timing Ti[s] differs from that of the first embodiment.

Operation

According to the present embodiment, the image-capture timing Ti[s] to be transmitted as a signal to a capsule endoscope 3 is derived from a predicted distance that the capsule endoscope 3 will travel.

Generally, a polynomial P(t) of degree n−1 is expressed as follows.

$$P(t)=a0+a1t+a2t^2+\ldots+an-1t^{n-1} \quad (3)$$

When three estimated positions Pi−2, Pi−1, and Pi of the capsule endoscope 3 are used, three coefficients a0, a1, and a2 in Expression (3) are obtained. For example, the following three equations with respect to the X direction are derived using Expression (3).

$$Xi-2(t0)=aX0+aX1t0+aX2t0^2$$

$$Xi-1(t1)=aX0+aX1t1+aX2t1^2$$

$$Xi(t2)=aX0+aX1t2+aX2t2^2 \quad (4)$$

The coefficients with respect to the X direction can be determined by solving the three simultaneous equations. Let t denote time obtained from image-capture timing.

Coefficients with respect to the Y and Z directions are similarly obtained, so that a predicted position P^i+1 of the capsule endoscope 3 shown in FIG. 8 can be calculated by the following Expression (the predicted position P^i+1 is a position after time t3).

$$X\hat{}i+1(t3)=aX0+aX1t3+aX2t3^2$$

$$Y\hat{}i+1(t3)=aY0+aY1t3+aY2t3^2$$

$$Z\hat{}i+1(t3)=aZ0+aZ1t3+aZ2t3^2 \quad (5)$$

The predicted position of the capsule endoscope 3 is obtained using Expression (5). A predicted distance D^i+1 shown in FIG. 8 is calculated using Expression (1). Substituting the calculated distance D^i+1 into Expression (2) gives the image-capture timing Ti[s].

The external device 5 transmits a signal indicating the obtained image-capture timing to the capsule endoscope 3. The capsule endoscope 3 generates a control signal for a CCD imager 17 to change the image-capture timing.

According to the present embodiment, the predicted position of the capsule endoscope 3 is obtained using a second degree polynomial. When a plurality of estimated positions of the capsule endoscope 3 are used, the position of the capsule endoscope 3 can be predicted more accurately. The position of the capsule endoscope 3 may be predicted using a spline function.

Advantages

In addition to the advantages of the first embodiment, the position of the capsule endoscope 3 is predicted, whereby image-capture timing at the predicted position can be accurately set.

Third Embodiment

Figure 9:
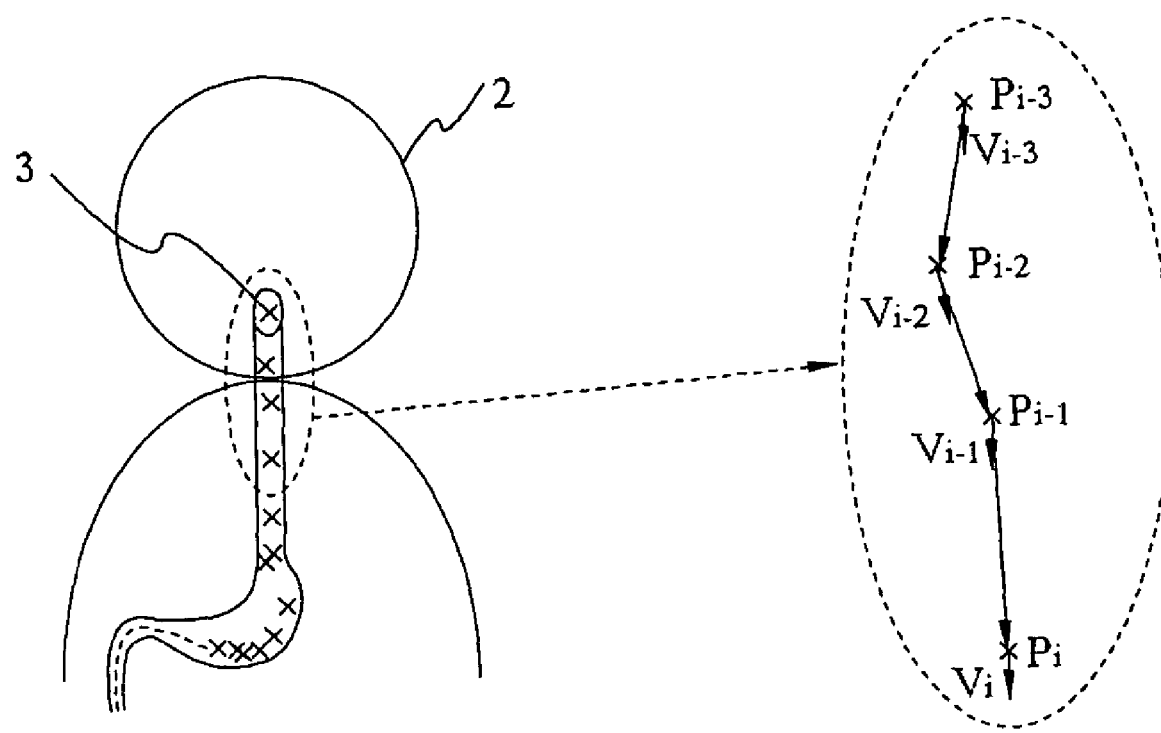
FIG. 9 is a diagram explaining a process by a signal processing circuit according to a third embodiment of the present invention.

FIG. 9 is a diagram explaining a process by a signal processing circuit according to a third embodiment of the present invention.

Structure

The structure of an apparatus according to the third embodiment is the same as that according to the first embodiment with the exception that a CPU in an external device 5 executes a process so as to control image-capture timing using information regarding the estimated orientation of a capsule endoscope.

Operation

As described in the first embodiment, the position and orientation of a capsule endoscope 3 can be estimated on the basis of strength signals received through antennas 11*ij*. As shown in FIG. 9, the orientation of the capsule endoscope 3 may not coincide with the moving direction thereof. When a distance that the capsule endoscope 3 has traveled is small and the orientation thereof is greatly changed, captured images may be different from each other in spite of the small distance.

The distance Di of the capsule endoscope 3 obtained in the first embodiment is derived from a distance between positions Pi=(Xi, Yi, Zi) and Pi−1=(Xi−1, Yi−1, Zi−1). Let Vi and Vi−1 denote the orientations at the respective positions. A change Δθ in orientation is expressed as follows.

$$\Delta\theta = \cos^{-1}\{Vi \cdot Vi-1/(|Vi| \times |Vi-1|)\} \quad (6)$$

where the operation "·" indicates the inner product of Vi and Vi−1 and |Vi| and |Vi−1| denote the magnitudes of vectors.

If the change Δθ in orientation of the capsule endoscope 3 is large, there is a lower likelihood that images in the same field of view are captured. Accordingly, image-capture timing of a CCD imager 17 in the capsule endoscope 3 is set to a higher rate. Image-capture timing Ti[s] can be calculated using the distance Di, the change Δθ in orientation, in the following Expression.

$$Ti = \alpha/Di + \beta \Delta\theta^{[s]} \quad (7)$$

where α and β are constants.

Advantages

In addition to the advantages of the first embodiment, advantageously, even when the distance that the capsule endoscope has traveled is small and the orientation thereof is drastically changed, the proper image-capture timing can be set by detecting a change in orientation.

Fourth Embodiment

Figure 10:
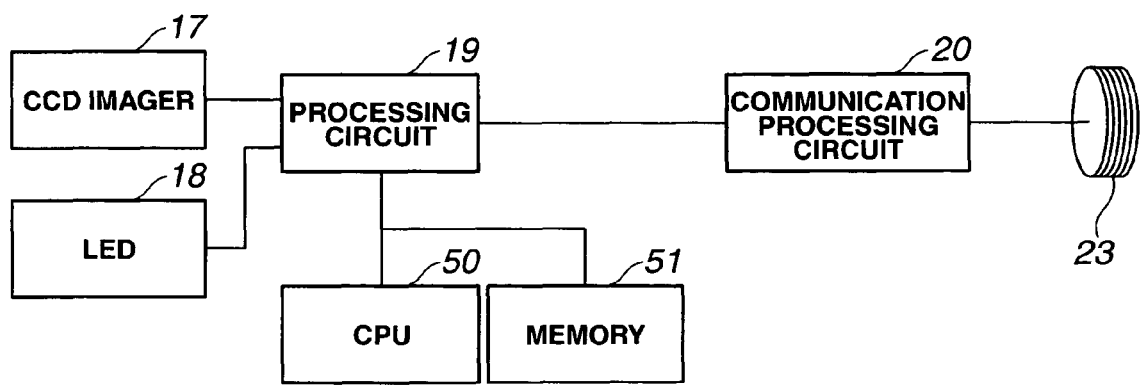
FIG. 10 is a block diagram showing the structure of an image capturing circuit of a capsule endoscope according to a fourth embodiment of the present invention.

FIG. 10 is a diagram showing the structure of a processing circuit of a capsule endoscope 3 according to a fourth embodiment of the present invention.

Structure

The structure of an apparatus according to the fourth embodiment is identical to that according to the first embodiment with the exception that a processing circuit 19 in the capsule endoscope 3 includes a calculation function realized by, e.g., a CPU 50 and a memory 51 as shown in FIG. 10.

Operation

Referring to FIG. 10, in the capsule endoscope 3, the processing circuit 19 includes the calculation function realized by the CPU 50 and the memory 51 and permits the capsule endoscope 3 to execute a program therein. In the first embodiment, the program is executed in the CPU and the memory included in the signal processing circuit 35 of the external device 5.

The capsule endoscope 3 transmits an image signal and a strength signal as shown in FIG. 5 at a predetermined radio-field intensity through an antenna 23 through a communication processing circuit 20. In an external device 5, a transmitting and receiving circuit 33 receives the signals through each of antennas 11ax, 11aY, . . . , 11dY, and 11dZ of an antenna unit 4.

The transmitting and receiving circuit 33 supplies the image signals and the strength signals to a signal processing circuit 35 to store the signals in memory means 47, such as a Compact Flash (registered trademark) memory (CF memory) or a hard disk, connected to the signal processing circuit 35. The signal processing circuit 35 supplies the strength signals received through the respective antennas 11ij to the transmitting and receiving circuit 33. The transmitting and receiving circuit 33 transmits the strength signal to the capsule endoscope 3 through the proper one of the antenna 11ij. As described in the first embodiment, the antenna most suitable to receive the image signal may be detected and, after that, the strength signal may be transmitted.

The capsule endoscope 3 receives the strength signal associated with the antenna 11ij transmitted from the external device 5 through the antenna 23 and the communication processing circuit 20 and supplies the received signal to the processing circuit 19.

The program for estimating the position and orientation of the capsule endoscope 3 using the strength signal received through the antenna 11ij connected to the external device 5 is installed on the CPU 50 and the memory 51 in the processing circuit 19 of the capsule endoscope 3. As described in the first embodiment, the CPU 50 utilizes the method for solving a plurality of nonlinear equations to estimate the position and orientation of the capsule endoscope 3, thus obtaining image-capture timing of a CCD imager 17 on the basis of the estimated position and orientation. The CPU 50 transmits data regarding the obtained image-capture timing to the processing circuit 19.

The processing circuit 19 generates a control signal to control image capture by the CCD imager 17, thus controlling image capture by the CCD imager.

Advantages

In addition to the advantages of the first embodiment, processes by the external device 5 can be distributed since a distance that the capsule endoscope 3 travels can be calculated in the capsule endoscope 3.

Fifth Embodiment

Structure

The structure of an apparatus according to a fifth embodiment is the same as that according to the fourth embodiment with the exception that an antenna 23 disposed in a capsule endoscope 3 detects a magnetic field generated by an antenna 11ij extracorporeally arranged.

Operation

A transmitting and receiving circuit 33 of an external device 5 generates a signal to permit antennas 11ij to generate magnetic fields having different frequencies. In response to the generated signal, the antennas 11ij generate respective magnetic fields having different frequencies. In the capsule endoscope 3, the antenna 23 receives the generated magnetic fields. The antenna 23 receives a signal obtained by combining signals having different strengths and frequencies. The received signal is subjected to band-pass filtering and gain adjustment through a communication processing circuit 20 and is then supplied to a processing circuit 19. The received signal supplied to the processing circuit 19 is digitized and is then stored in a memory 51 connected to a CPU 50. The CPU 50 performs frequency extraction (Fourier transform: FET) on the received signal stored in the memory 51 to obtain signal strengths corresponding to the magnetic fields generated by the respective antennas 11ij.

A program for estimating the position and orientation of the capsule endoscope 3 as described in the fourth embodiment is installed on the capsule endoscope 3. Accordingly, the position and orientation of the capsule endoscope 3 are estimated using signal strengths corresponding to the respective antennas 11ij. A distance is calculated using the estimated position and orientation, whereby image-capture timing of a CCD imager 17 is obtained. Data regarding the obtained image-capture timing is transmitted to the processing circuit 19. The processing circuit 19 generates a control signal to control image capture by the CCD imager 17, thus controlling image capture by the CCD imager 17.

In the capsule endoscope 3, the communication processing circuit 20 converts information regarding the position and orientation obtained by the CPU 50 and a captured image signal into a signal that can be transmitted from the antenna 23. The antenna 23 transmits the signal. The signal transmitted from the antenna 23 is supplied to the transmitting and receiving circuit 33 through the antennas 11$ij$ connected to the external device 5. A signal processing circuit 35 converts the signal into a signal that can be stored in memory means 47. The memory means 47 stores the signal.

Advantages

In addition to the advantages of the fourth embodiment, power consumption of button batteries 21 for supplying power can be reduced since the antenna of the capsule endoscope 3 can detect external magnetic fields.

Sixth Embodiment

Figure 11:
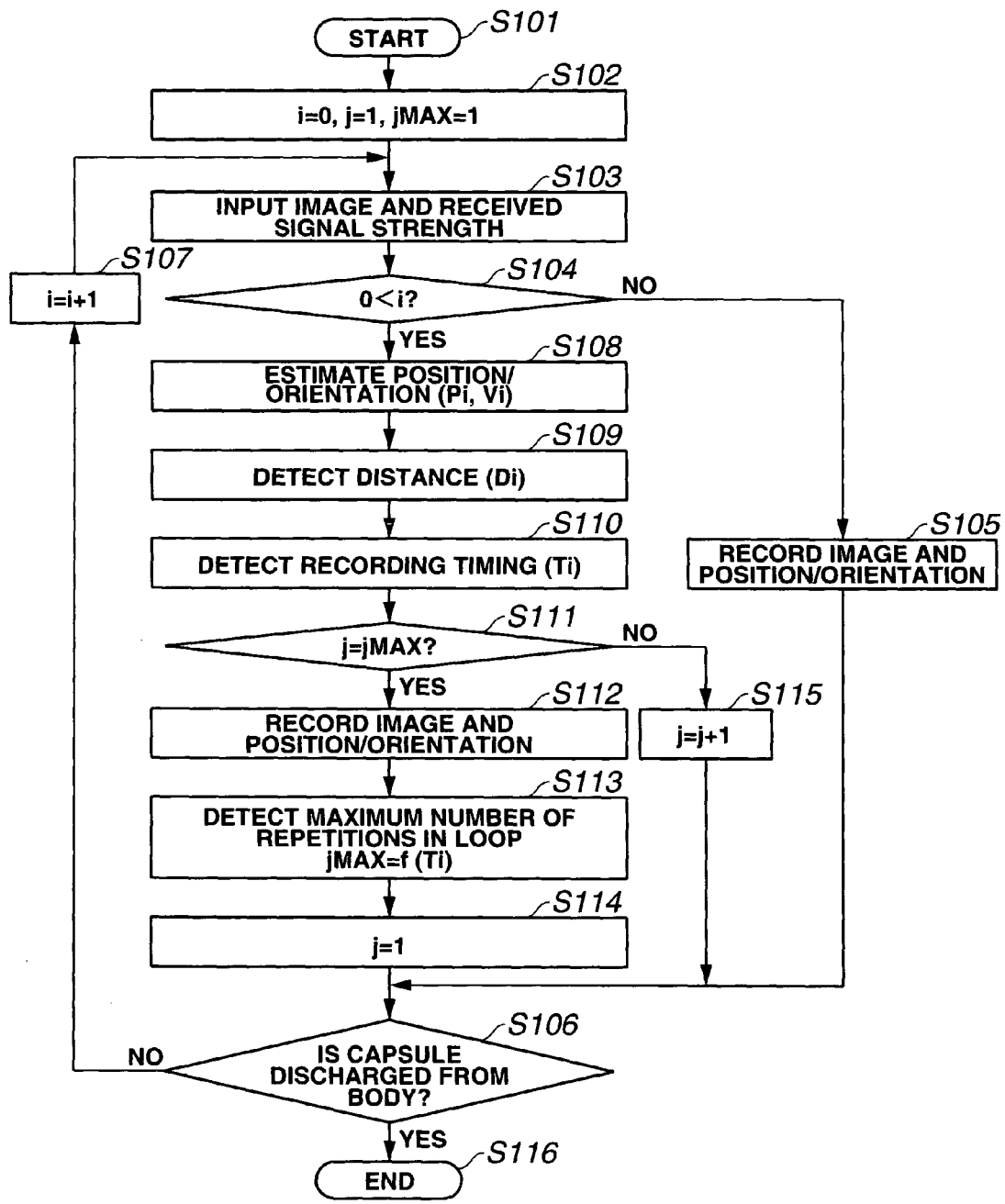
FIG. 11 is a flowchart showing the flow of a process executed by a signal processing circuit in an external device according to a sixth embodiment of the present invention.

FIG. 11 is a flowchart showing the flow of a process by a signal processing circuit of an external device according to a sixth embodiment of the present invention.

Structure

The structure of an apparatus according to the sixth embodiment is the same as that according to the first embodiment with the exception that recording of an image signal and information regarding the position/orientation of a capsule endoscope 3 on memory means 47 of an external device 5 is controlled in accordance with a distance that the capsule endoscope 3 has traveled.

Operation

The capsule endoscope 3 transmits an image signal and a strength signal as shown in FIG. 5 at a predetermined radio-field intensity through an antenna 23. In the external device 5, a transmitting and receiving circuit 33 receives the signals through each of antennas 11$ax$, 11$aY$, ..., 11$dY$, and 11$dZ$ of an antenna unit 4.

A signal processing circuit 35 of the external device 5 includes a CPU and a memory which are not shown. The image signal and the strength signal, transmitted from the capsule endoscope 3 and received through each antenna 11$ij$, are recorded on the memory means 47 in accordance with a program corresponding to the flowchart shown in FIG. 11.

When the capsule endoscope 3 is inserted into a body, the signal processing circuit 35 starts the program corresponding to the flowchart shown in FIG. 11 from step S101. In step S102, variables i, j, and jMAX are initialized such that i=0, j=1, and jMAX=1.

In step S103, an image signal and a strength signal received through any antenna 11$ij$ are given to the program. If it is determined in step S104 that the variable i is smaller than 0, the image signal and the received signal strength are recorded on the memory means 47 in step S105.

Subsequently, the process proceeds to step S106, in which it is determined whether the capsule endoscope 3 is discharged from the body. If the capsule endoscope 3 exists in the body, the process proceeds to step S107, in which the variable i is incremented. When the capsule endoscope 3 is discharged from the body, the process proceeds to step S116, thus terminating the program.

When the variable i is incremented in step S107, the process proceeds to step S103, in which the next image signal and strength signal are given to the program. If it is determined in step S104 that the variable i is larger than 0, the process proceeds to step S108. 12 nonlinear equations, in which the position and orientation of a single-core coil arranged in the capsule endoscope 3 are unknown, are obtained using the signal strengths of the strength signals received through the antennas 11$ax$, 11$aY$, ..., 11$dY$, and 11$dZ$. The 12 nonlinear equations are solved by iterative refinement, e.g., the Gauss-Newton method, whereby the position and orientation of the capsule endoscope 3 are estimated.

Next, in step S109, a distance Di is calculated using Expression (1). In step S110, recording timing Ti[s] is calculated using Expression (2). If it is determined in step S111 that the variable j is equal to the specific value jMAX, the process proceeds to step S112, in which the image signal and strength signal are recorded on the memory means 47. The process then proceeds to step S113, in which an image recording interval is obtained from the recording timing Ti[s].

For example, when 10 frame images are transmitted from the capsule endoscope 3 for one second and the recording timing Ti is calculated as 0.5 [s], one out of every five images is recorded (jMAX is set to 5).

In step S114, the variable j is initialized. In step S106, whether the capsule endoscope 3 exists in the body is determined.

If it is determined in step S111 that the variable j is different from the specific value jMAX, the process proceeds to step S115, in which the variable j is incremented.

According to the present embodiment, the image recording interval is obtained. Each image, which is not to be recorded, may be recorded with information regarding the position and orientation by compressing image data or reducing the size of the image or converting the data into information, such as an icon. For example, when the recording interval is set to five frames, four frame images, which are not to be recorded, may be recorded on the memory means 47 together with information regarding the position and orientation such that the size of each image is reduced.

Advantages

In addition to the advantages of the first embodiment, a distance that the capsule endoscope has traveled in the body is obtained with accuracy and images are recorded. Advantageously, a user can efficiently confirm a diagnosis using the images.

Seventh Embodiment

Figure 12:
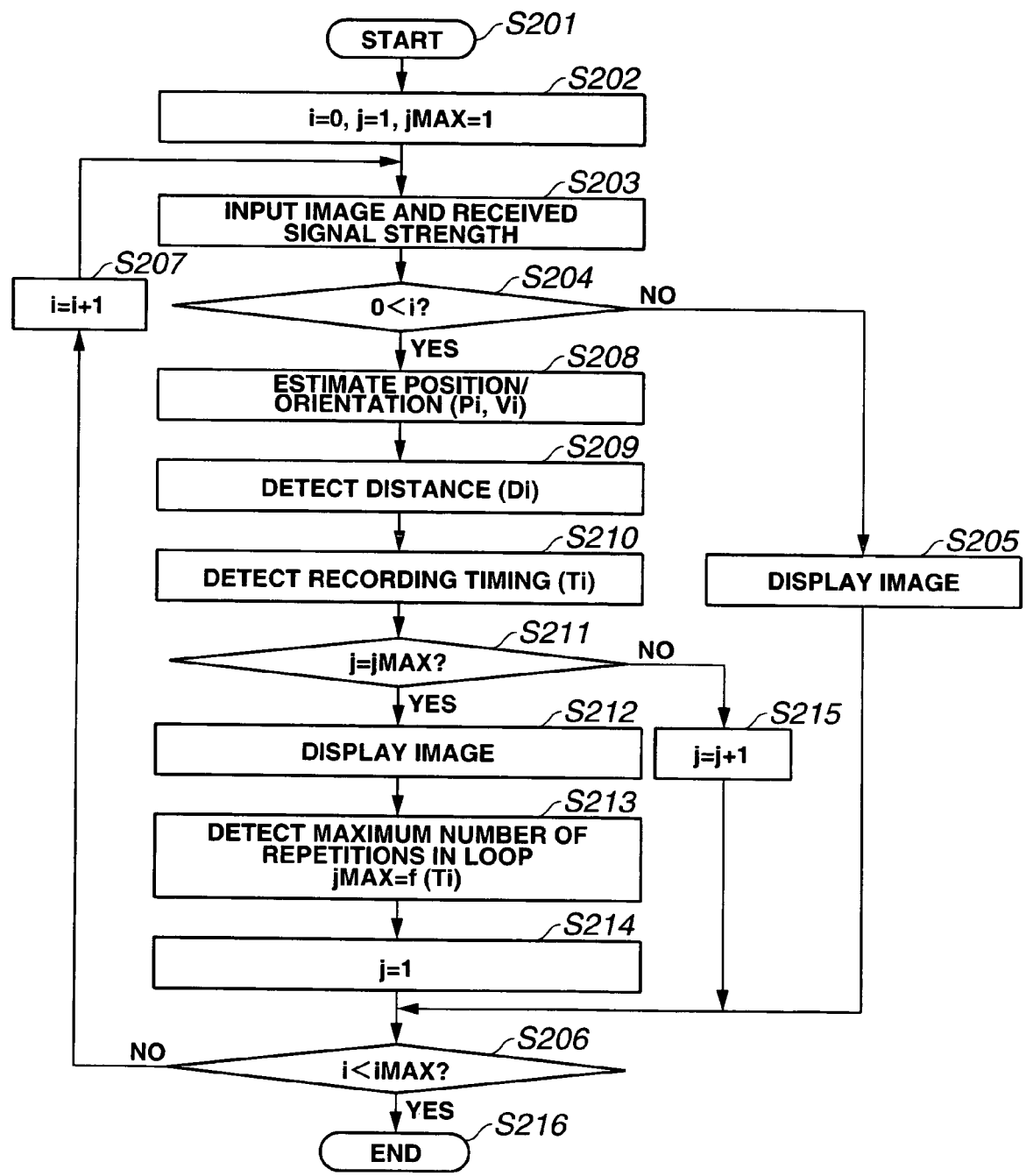
FIG. 12 is a flowchart showing the flow of a process performed by a terminal according to a seventh embodiment of the present invention.
Figure 13:
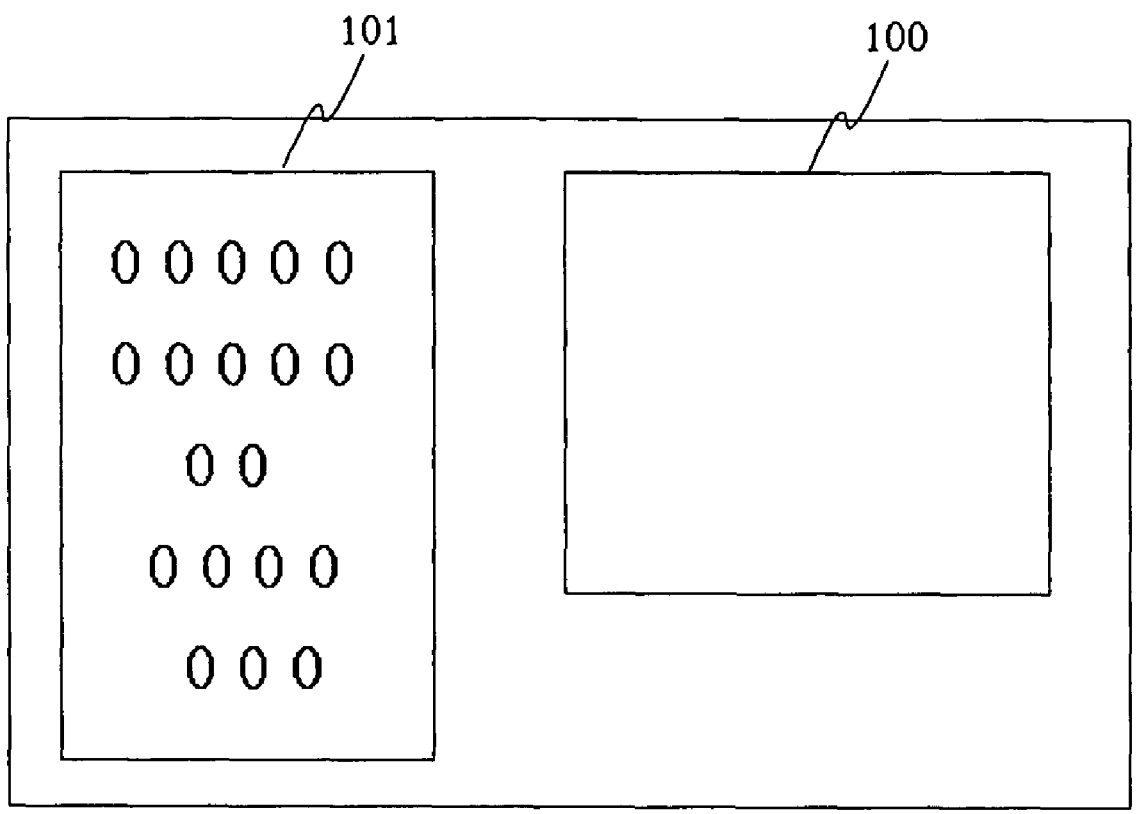
FIG. 13 is a first diagram showing an example of a screen displayed on the terminal by the process of FIG. 12.
Figure 14:
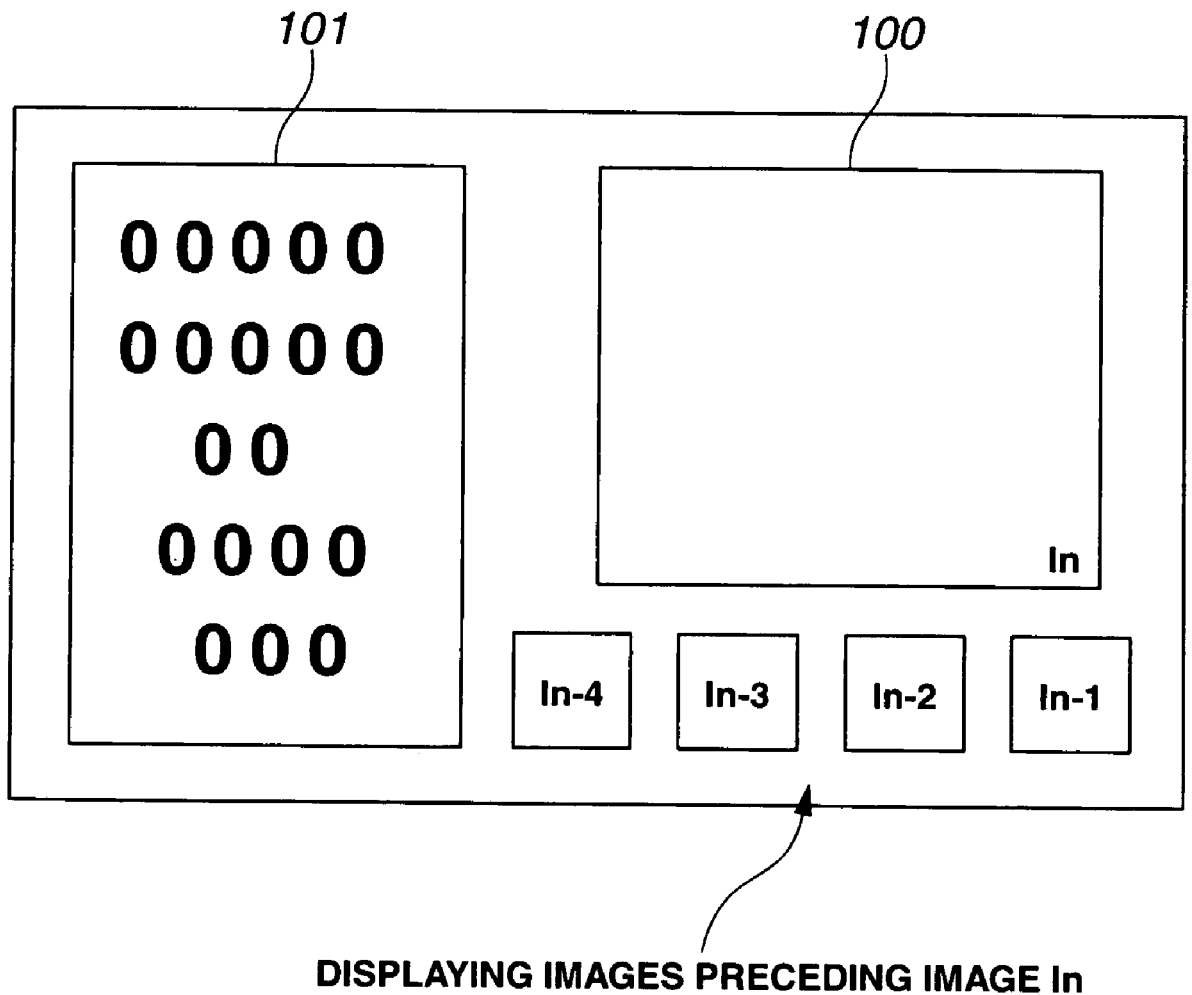
FIG. 14 is a second diagram showing an example of a screen displayed on the terminal by the process of FIG. 12.

FIGS. 12 to 14 relate to a seventh embodiment of the present invention. FIG. 12 is a flowchart showing the flow of a process by a terminal. FIG. 13 is a first diagram showing an example of a screen displayed on the terminal by the process of FIG. 12. FIG. 14 is a second diagram showing an example of a screen displayed on the terminal by the process of FIG. 12.

Structure

Since the seventh embodiment is substantially identical to the first embodiment, only the difference therebetween will now be described. The same components are designated by the same reference numerals and a description of the previously described components is omitted.

Operation

As shown in FIG. 4, a capsule endoscope 3 transmits an image signal and a strength signal as shown in FIG. 5 at a predetermined radio-field intensity through an antenna 23. In an external device 5, a transmitting and receiving circuit 33 receives the signals through each of antennas 11$ax$, 11$aY$, ..., 11$dY$, and 11$dZ$ of an antenna unit 4.

The transmitting and receiving circuit 33 supplies the image signals and strength signals to a signal processing circuit 35. The signal processing circuit 35 compares strength levels of the strength signals received through the respective antennas 11$ij$. Consequently, the signal processing circuit 35 detects the antenna most suitable to receive the image signal transmitted from the capsule endoscope 3. The signal processing circuit 35 supplies the image signal obtained through the most suitable antenna and the strength signals received through the respective antennas 11$ij$ to memory means 47, such as a Compact Flash (registered trademark) memory (CF memory) or a hard disk, connected to the signal processing circuit 35 to store the signals.

When observation in a body through the capsule endoscope 3 is finished, the image signals and strength signals recorded on the memory means 47 of the external device 5 are transferred to recording means in a terminal 7.

The terminal 7 includes a CPU and a memory, which are not shown, whereby application software for displaying images is executed through a user interface, such as a keyboard or a mouse, connected to the terminal 7.

When the application software is executed, in the terminal 7, a program corresponding to the flowchart shown in FIG. 12 starts from step S201. In step S202, variables i, j, and jMAX are initialized such that i=0, j=1, and jMAX=1. In step S203, an image signal and a strength signal of any antenna 11$ij$ are read from the recording means and are then given to the program. If it is determined in step S204 that the variable i is smaller than 0, the image signal is displayed on display means, such as a monitor, in step S205.

Next, the process proceeds to step S206, in which it is determined whether all of the image signals and strength signals have already been read out. If any unread image and strength signals exist, the process proceeds to step S207, in which the variable i is incremented. When all of the image and strength signals have already been read, the process proceeds to step S216, thus terminating the program.

When the variable i is incremented in step S207, the process proceeds to step S203, in which the next image signal and strength signal are read out from the recording means and are then given to the program. If it is determined in step S204 that the variable i is larger than 0, the process proceeds to step S208. 12 nonlinear equations, in which the position and orientation of a single-core coil arranged in the capsule endoscope 3 are unknown, are obtained using strength levels of the strength signals received through the antennas 11$ax$, 11$aY$, . . . , 11$dY$, and 11$dZ$. The 12 nonlinear equations are solved by iterative refinement, e.g., the Gauss-Newton method, thus estimating the position and orientation of the capsule endoscope 3.

Thereafter, in step S209, a distance Di is calculated using Expression (1). In step S210, display timing Ti[s] is calculated using Expression (2). If it is determined in step S211 that the variable j is equal to the specific value jMAX, the process proceeds to step S212, in which the corresponding image is displayed on the display means, such as a monitor. The process then proceeds to step S213, in which an image display interval is obtained on the basis of the display timing Ti[s].

For example, when 10 frame images are recorded on the recording means for one second and the display timing Ti is calculated as 0.5 [s], one out of every five images is displayed (jMAX is set to 5).

In step S214, the variable j is initialized. In step S206, it is determined whether all of the image signals and strength signals have already been read.

According to the present embodiment, an image may not be displayed as a moving picture depending on display timing. In this case, as shown in FIG. 13, an image, which is not displayed as a moving picture, may be displayed in an area 101 separated from a moving picture display area 100. Alternatively, as shown in FIG. 14, images may be reduced or be displayed in a different form, e.g., as icons.

Advantages

According to the present embodiment, a distance that the capsule endoscope 3 has traveled is obtained with accuracy and images are displayed. Advantageously, a user can efficiently confirm a diagnosis using the images.

In the present invention, it will be apparent that a wide range of different embodiments can be formed based on this invention without departing from the spirit and scope of this invention. The present invention will be restricted by the appended claims but not be limited to any particular embodiment.

What is claimed is:

1. A capsule endoscope apparatus comprising:
an image capturing unit for capturing an image in a body to transmit the image by radio;
a receiving unit for receiving the image and a strength signal transmitted by radio from the image capturing unit and for recording the image in a memory operatively connected to the receiving unit;
an estimating unit for receiving the signal transmitted by radio from the image capturing unit through each of a plurality of antennas arranged at different positions outside the body to estimate the position and orientation of the image capturing unit on the basis of the signals received through the antennas;
a control unit for setting a display interval of the images recorded by the receiving unit based on information regarding the position and orientation obtained by the estimating unit, and controlling display of the images recorded by the receiving unit according to the display interval; and
a display unit for displaying the images under the control of the control unit;
wherein the control unit includes:
a distance calculating unit for calculating a distance that the image capturing unit has traveled on the basis of a plurality of positions of the image capturing unit obtained by the estimating unit;
an orientation-change calculating unit for calculating a change in orientation of the image capturing unit on the basis of a plurality of orientations obtained by the estimating unit; and
a display control unit for setting the display interval of the images recorded by the receiving unit on the basis of the distance and the change in orientation.

2. The capsule endoscope apparatus according to claim 1, wherein the distance calculating unit includes a unit for calculating a predicted distance on the basis of the plurality of positions of the image capturing unit obtained by the estimating unit.

3. The capsule endoscope apparatus according to claim 2, wherein the predicted distance is calculated using an approximation function derived from the plurality of positions of the image capturing unit obtained by the estimating unit.

* * * * *